United States Patent [19]

Lucki et al.

[11] 4,265,619
[45] May 5, 1981

[54] METHOD AND APPARATUS FOR PROCESSING DENTAL MODELS

[75] Inventors: John L. Lucki, Edison, N.J.; Alan B. Naha, Parma, Ohio

[73] Assignee: Dental Essentials, Inc., Edison, N.J.

[21] Appl. No.: 55,502

[22] Filed: Jul. 9, 1979

[51] Int. Cl.³ .......................................... A61C 11/00
[52] U.S. Cl. ..................................... 433/54; 433/74; 433/213
[58] Field of Search ...................... 433/60, 213, 54, 74

[56] References Cited

U.S. PATENT DOCUMENTS

| | | | |
|---|---|---|---|
| 2,545,249 | 3/1951 | Ackerman | 433/72 |
| 2,619,725 | 12/1952 | Roeser | 433/60 |
| 2,786,272 | 3/1957 | Lindley | 433/60 |
| 2,801,570 | 8/1957 | Logan et al. | 433/67 |
| 2,911,722 | 11/1959 | Benfield et al. | 433/60 |
| 3,043,009 | 7/1962 | Whitman | 433/49 |
| 3,581,398 | 6/1971 | Thomas | 433/74 |
| 3,704,519 | 12/1972 | Lystager | 433/213 |
| 3,838,187 | 9/1974 | Thomas | 264/17 |
| 3,932,939 | 1/1976 | Weissman | 433/213 |
| 4,083,114 | 4/1978 | Aceuedo | 433/2 |

*Primary Examiner*—Robert Peshock
*Attorney, Agent, or Firm*—Martha G. Pugh

[57] ABSTRACT

A method and apparatus for processing cast models, such as dental molds and for various other applications, which comprises two separate sections, each having on its male and female seating or mating surface an assortment of geometric patterns of various sizes, depths and protrusions, prefabricated as a mating sandwich on which a hardened model, such as of teeth, gum or jaws, can be attached without the manipulation of unhardened moulding compounds, and/or mechanical aids, to obtain a working platform and precision reference apparatus essential in constructing parallel working dies.

28 Claims, 8 Drawing Figures

METHOD AND APPARATUS FOR PROCESSING DENTAL MODELS

BACKGROUND OF THE INVENTION

This invention relates in general to the precision mating of two elements, more particularly, to the making of cast models, such as for the precise fabrication of models of teeth, gums and jaws.

The prior art method for fabricating dental models necessitates the conventional manipulation of a patient's negative impression to ultimately obtain a positive model with removable tooth segments and dies. In prior art practice, many time-consuming steps and much skill is required to manually set various types of pins into the tooth, gum or jaw facsimile. This requires interposing bushings, sleeves or guides into matching holes which are usually incorporated into a base. It is customary to construct the latter at the time the model is poured, using gypsum, epoxy, putty or other moulding materials.

Prior art methods for constructing crowns, inlays, bridges, dentures, etc., either in composite or individually, necessitate the ability to remove each individual segment (tooth-die) from its spatial physical relationship to the remainder of the jaw model for the purpose of constructing accurate margins and contours. In the event that two or more individual units of bridgework are to be joined, either by a one piece casting, solder joint, sticky-wax, coping, or a precision attachment, it is necessary that the working model segments be accurately and repeatedly returned to their original relationships precisely as it or they existed prior to any cutting, separations or disassembly of the jaw model.

In prior art practice, such working models are constructed by the following tedious, inefficient and precious-time consuming steps:

(1) Painstakingly placing a pin, pins, or bushings into or over the negative cavity of the tooth in the impression by "eyeballing" and guaging it with respect to the vertical axis of each adjacent negative tooth cavity while avoiding physical contact with the patient's negative mouth impression or adjacent pins;

(2) Using some method (normally a cross-wire, hot wax, a holding mechanism or other gadget) to "freeze" the pin or sleeve in the position it was placed; and (3) Pouring liquid gypsum or other setting material into the mold and waiting for it to polymerize, crystalize, set or harden. The so-called "first pour" then hardens thereby imprisoning the pins, sleeves or bushings rigidly, as they were placed or positioned manually, mechanically, visually or otherwise.

(4) After these pins or devices are set rigidly in position by the hardening of the first pour, a releasing, anti-seizing or separating medium must first be carefully coated over the gypsum or whatever was used as a moulding compound. This permits essential future separation, and a second pour is then made.

(5) After the second pour hardens, the working model is removed from the original negative impression, prepared for placement or acceptance on an articulator platform and sectioned. Sectioning facilitates the removal and consequent replacement of the individual dies. On occasion, during their removal, or during efforts to effect separation, the two halves fracture or break apart and the formerly rigid pins either bend, loosen, collapse, or dislodge due to loss of perimeter support.

Common methods presently used in the construction of such models require the skillful and experienced application of judgment in the positioning of pins or guides, either manually or mechanically, the use of unhardened liquid moulding materials, such as for example, gypsum, and the "trial and error" positioning of pins, bushings or dressed models to capture the desired location and parallelism. Therefore, a working time limit and "critical" situation is established. If any step is affected by either judgmental or mechanical error, defective materials such as faulty, nonhomogeneous, or contaminated mixtures, etc., or environmental influences, such as temperature, moisture, or the inadvertent movement, dislodgement or displacement of the pins or guides during pouring, the entire procedure fails. This necessitates the dentist taking a second impression of the patient's teeth, gum, jaw or mouth (a situation professionally embarrassing and uncomplimentary, since it extends extra imposition and inconvenience to the patient, requiring a revisit to the dentist's office).

Whatever methods are in use or utilized in the prior art, the following problems consistantly exist:

(1) "Eyeballing", the use of gadgets, mechanical devices or other apparatus are required on the part of the operator to properly align the reference pins. The methods used are tedious, time consuming, expensive and inefficient.

(2) Unhardened gypsum or other moudling compounds are normally required for the process of securing incorporated male and female "pins" or bushings in preparing models. These systems at best are difficult to control, and are oftentimes nonreversible.

(3) Critical and time-expensive setbacks occur in the nature of such methods, such as difficulty in establishing parallelism of two or more segments, in keeping deep female sections free of often unavoidable foreign debris, not to mention shrinkage, warpage, fusing, the wear of gypsum or other materials which harden during the procedure.

(4) Inadvertent separation of the two adjacent sections may occur in a model thinly held together by virtually only the metal or plastic locating or positioning pins, thereby causing the entire first and second pours to be separated from the impression material.

It is therefore a broad object of this present invention to improve the entire fabrication of cast models, and more particularly of model teeth, gums and jaws.

A more particular object of this invention is to facilitate the removal and precise return of individual segments of a hardened dental casting to its or their original positional relationship, during processing.

Other objects of this invention are to eliminate the tedious and painstaking manipulation of pins, bushings, guides, mechanical aids, or the use of other expedients, such as hot wax, sprues, mechanical holding devices, other gadgets, or the successive pourings of setting materials into the mold for the purpose of securing reference-type aids or elements for the casting.

These and many other objects are realized in the present invention which comprises a prefabricated sandwich which is constructed to accept a cast model such as of teeth, gums and jaws. In preferred form, this sandwich consists of a pair of precision plates including a mounting plate and lower mating plate and into the mating surfaces of which are incorporated a profuse and extended interdigitation of geometric patterns of varying depths and sizes. The hardened model of the jaw is merely glued, fastened or otherwise secured to the mounting plate for processing. The remaining half, or lower mating plate, forms its base.

In accordance with this present invention, the precision plates of the pair are preferably formed so as to be completely interchangeable (any upper mounting plate fitting any lower mating plate). They invariably mate together snugly to provide a fixed registration. Unrestricted compound cuts and required separations may be executed on the cast model clean through the plate section upon which the model is fastened without destroying the segment's replacement accuracy. Since each half or individual plate of the mating sandwich is precisely fabricated by the manufacturers in advance, and constructed of durable materials, they are not subject to technician or operator error. Normal environmental factors such as temperature, humidity, nonhomogeneous gypsum or other moulding mixes, or foreign contaminents in dirty water may no longer be of concern. No pins, bushings, sleeves, drilling or boring by mechanical means and other similar procedures are any longer required in the construction of dies of the types described. The original precision mating fit of the mating plates remains constant throughout the entire working procedure.

After the hardened model of the teeth is secured to the proper surface of the precision mating plates of the present invention, the individual teeth and edentulous areas, if applicable, are sectioned only as far as needed to permit cutting through the mounting plate. The lower mating plate need not be cut or sawed into. In fact, the model, complete with the fastened upper mounting plate, may be lifted clear of the lower mating plate and placed to the side; and separation by cutting or sawing may be carried out in this manner. With the use of this highly versatile device, each and every section is immediately contiguous with each other section; therefore, any quadrant or an entire half a section of the "arch-model", once it's fastened to the mounting half section of the precision mating plates, may be cut through and removed from the line of saw or cutting blade travel if it appears that it will be in the way or an obstacle during the course of starting cuts or separations on the opposite side or section.

All, and any individual segments, quadrants, or half sections can also be removed individually, or simultaneously, as needed, from an entire upper or entire lower dental plate, for trial of a one-piece bridge consisting of two or more units, or for soldering. With prior art methods, this is not as readily or as easily possible. The structure of the present invention also facilitates mounting and repositioning the various elements or composites to articulators. The lower mating plate has a configured geometric pattern and a keyed protuberance incorporated on the underside for engagement by whatever method of fastening, bonding, holding, latching, or clamping that one may elect to utilize. For example, gypsum, plasters, glues, adhesives, or mechanically designed key-ways, clamps, latches or magnetic assisting or adhering devices may be chosen.

In accordance with another feature of the present invention, the precision mating plates may be provided with built-in venting openings to the underside of each of the elements of a pattern to eliminate the inadvertent or sporadic possible trapping of debris inside the geometric patterns which might otherwise prevent their precise seating or joining. As a further feature to facilitate accuracy, the mating plates may be keyed, indexed and/or color coded on their inner and/or outer perimeter edges, so that an immediate visual identification permits placement of appropriate segments or sections to the correct quadrant or location without "trial and error" locating techniques. Also, notchings may be provided around the outer edges in between the two mating plates which may serve to assist in the quick removal and separation of individual sections when needed. A further desirable feature which may be incorporated as part of the combination of the present invention is a slightly extended overhang of adequate cross section located along the outer and inner perimeter of the upper mounting plate that holds the model. This feature not only provides a grasping ledge which permits the operator to avoid excessive fingering of the work die on its critical surface areas, but it also helps avoid rocking or prying adjacent segments off their respective seats.

Applicant's device has a multitude of advantages over prior art methods, gadgets and apparatus available for prefabricating the processing cast models, particularly models of teeth, gums, and jaws. Once any model, be it teeth, gum or jaw section, has been attached or fastened to the mounting plate, individual sections can be promptly cut, removed and worked upon an indefinite number of times and precisely replaced in exact spatial relationship to the other elements of the model as it originally existed, without need for the exercise of constant caution, care and anxiety on the part of the operator, and without the detrimental wear and tear and consequent loss of accuracy due to looseness developing in one or more individual die segments.

Other objects, features and advantages will readily appear to those skilled in the art after a study of the detailed description hereinafter with reference to the attached drawings.

DETAILED DESCRIPTION OF THE INVENTION

The method and apparatus of the present invention will be described with particular reference to their specific application to the making of dental models, although it will be understood that the principles of the present invention can be applied to the making of many other types of cast models.

The first step in making a dental model is to make an impression of the relevant portions of the patient's tooth, gum or jaw structure. In accordance with well-known prior art procedure, this is carried out by placing a tray of dental impression material in the patient's mouth. When the material has set, the tray is removed. The impression material now shows a negative outline of the subject's teeth, gum, or jaw. Gypsum or other moulding material is then poured into the impression and allowed to harden. The hardened model is then separated from the impression to provide a working model of the patient's teeth, gum or jaw. The patient's model is then attached by suitable bonding means, such as, for example, a cement sold by the DuPont Companies under the trademark DUCO, to a base element which is mounted on an articulator.

The articulator is a device comprising upper and lower mounting platforms which may be connected in a variety of manners on the inside to receive the upper and lower jaw elements and to simulate the relationships or the actual movement or bite of the human jaw.

During the procedure for constructing dental appliances, it is necessary for the dentist, dental technician or operator to be able to remove an individual segment of the model from its spatial relationship with the remainder of the jaw model in order to construct accurate margins and contours, and to replace the removed section to true and precise spatial relationship to the remaining portions of the jaw model. As previously pointed out, the prior art method for doing this involved a tedious procedure in which one or more pins or bushings were positioned in the tooth cavity on which the operator wished to work, perpendicular to the long axis of the model, by visual positioning and held in place by wires, such as bobby pins. After one or more additional pours, the gypsum model could be separated from the impression, and cut at the desired place, so that the tooth model could be removed, worked on, and returned to its proper location. It is apparent that the accuracy and efficiency of this method leaves much to be desired. The repeated removal and replacement of segments tends to erode the original fit and position of the pin so that is precise relationship no longer exists and collective alignment accuracy is no longer possible.

Referring to FIGS. 1-4 of the drawings, the articulator 1, to which casts of the jaws are conventionally attached during the process of preparing false teeth, or bridges, crowns, inlays and the like, has upper and lower supporting platforms 2 and 3 which are arranged to open and close about a hinge 1a.

Figure 1:
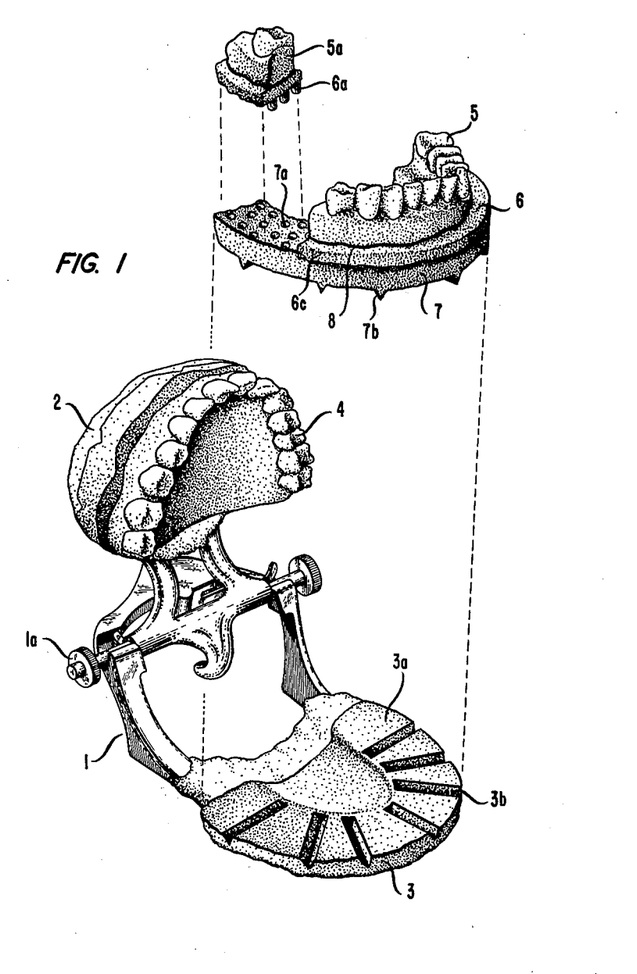
FIG. 1 shows an articulator including a hardened upper jaw model mounted thereon, and an exploded view of a lower jaw model mounted in accordance with the present invention to include a lower mating plate disengaged from the patterned supporting base of the articulator, and an individual tooth segment disengaged from the geometrically patterned lower mating plate.
Figure 2:
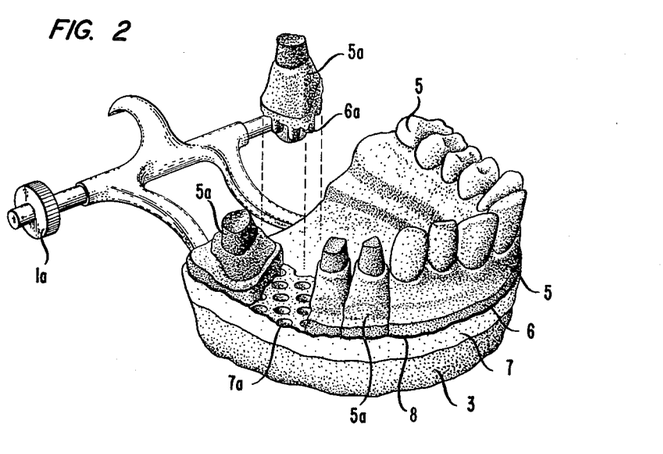
FIG. 2 is a perspective view, looking from one side, of the lower jaw model mounted on the articulator with one tooth sector removed from mating relating with the lower mating plate.
Figure 3:
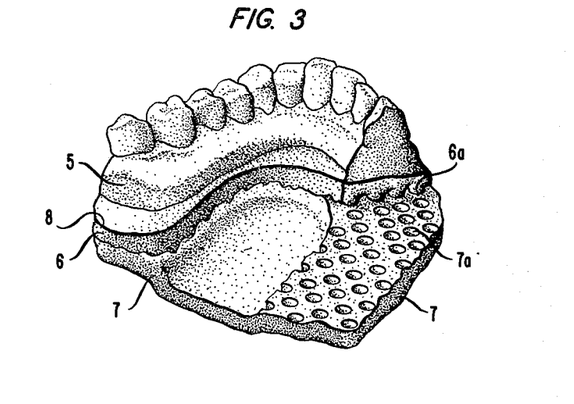
FIG. 3 is an inside perspective view, looking down from above, of a lower jaw model in accordance with the present invention, showing a portion of the geometrically patterned lower mating plate with several sectors of individual tooth models removed therefrom.
Figure 4:
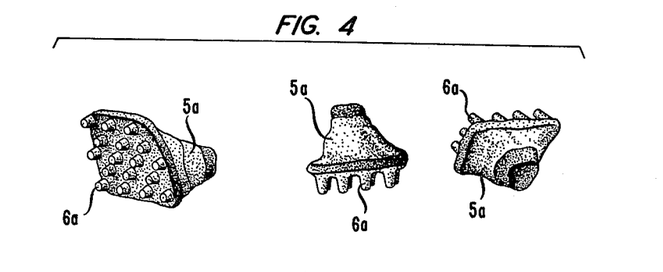
FIG. 4 are perspective views, respectively from the bottom, side, and top, of an individual tooth sector showing the geometrically shaped projections designed to mate with the exposed portion of the lower mating plate FIG. 3 from which it was removed.

In FIG. 1, the upper jaw model 4, (which to simplify the description is shown as permanently secured by plastering, but which may alternatively be assembled as taught in accordance with the present invention, and as described hereinafter with reference to the lower jaw model 5) is mounted in a downwardly-projecting manner from the articulator platform 2.

FIG. 1 shows, in exploded view, the lower jaw model 5 which is constructed for mounting on the lower platform 3 of the articulator 1. As shown in the exploded view, the bottom surface of gypsum jaw model 5 is bonded with an adhesive cement, epoxy, or the like, to the substantially plain upper surface of mounting plate 6, forming a rigid bond 8. The lower surface of mounting plate 6, which, in accordance with the present invention is covered with an elaborate and abundant interdigitation of geometric patterns 6a of varying depths and sizes, is constructed to mate with inverse patterns 7a on the upper surface of the lower mating plate 7. The plates 6 and 7 are preferably formed of a suitable blend of injection molding resin, such as, for example, a commercially available formulation of acrylonitrile butadiene styrene, (known as ABS) but can be formed of any rigid thermoplastic material such as a high impact polymer resin which can be permanently molded (preferably by injection molding) to a precision of within approximately one thousandth (0.001) of an inch, has a Rockwell (R) hardness number within the range 75-150, and a flexural modulus (when hardened) within the range 200,000-600,000 p.s.i.g.

It will be understood that, in addition to rigid plastics and rigid polyurethane, other acceptable or suitable thermoplastic or thermosetting materials, such as, but not limited to, an epoxy, acrylic, polyester, nylon, polyacetal, or a thermoset resin such as phenol formaldehyde, can be used for the purposes of the present invention.

The botton surface of 7 may also be embossed and configured with a pattern 7b, which is less elaborate than pattern 7a and which is so formed that it meshes with a pattern 3a on the surface of supporting platform 3. In the presently described embodiment, the supporting platform 3 is engraved on its upper surface 3a with a plurality of radially-directed grooves 3b of triangular cross-section which are constructed to accommodate the projections 7b on the lower surface of lower mating plate 7. If desired, any adequate and acceptable adhesive, suitable bonding method, or mechanical or other suitable securing means may be interposed at this point to retain supporting plate 7 fixed to platform 3. In the present illustrative embodiment, a rubber based solvent contact adhesive has been found suitable.

After the gypsum model 5 has been hardened and bonded to mounting plate 6, and the bond 8 has hardened, one or as many cuts as needed may be made vertically, through the gypsum model 5 and the mounting plate 6 to form isolated segments 5a, which may comprise a single tooth, or which may correspond to a section of jaw, so that the dentist or technician may remove segments such as 5a from the supporting plate 7. Because of the intermeshing geometric patterns 6a and 7a, the segment 5a may be replaced with true precision in the exact location from which it was removed.

It will be understood that the intermeshing patterns 6a-7a may take many different geometric forms and shapes. For example, as shown in FIGS. 1-4 the patterned surface 6a may take the form of a plurality of projections, each projection being slightly frustoconical, say 0.060 inches across the base, and 0.030 inches across the top, and extending out 0.220 inches from the surface, the centers of adjacent projections being separated, by say, 0.200 inches. The mating surface 7a may comprise a plurality of frustoconical recesses separated and shaped to exactly accommodate the projections on 6a. In addition, it is contemplated that the recesses on 7a may be extended through the thickness of 7 forming small perforations in order to facilitate the removal of moulding particles, dirt, debris, or other contaminents which might otherwise collect in the recesses on 7a.

It is contemplated that many different types of geometric patterns might be substituted for the patterns 6a and 7a shown in FIGS. 1-4. For example, alternative intermeshing patterns 6a' and 7a' are shown for the mounting plate 6' and the lower mating plate 7', in FIGS. 5 and 6, respectively. It will be seen that the mating surfaces may comprise a number of different interlocking planes; and the supporting plate 7' and the mounting plate 6' may each comprise projections and recesses which are designed to exactly and precisely mesh with recesses and projections in the corresponding position in the other. For example, in an alternative form shown in fragment in FIG. 7, the plate 7' may include a plurality of frustoconical projections 10 which are designed to protrude into recesses in plage 6'; but these are much shorter than the vertical, downward projections on 6a'.

Figure 5:
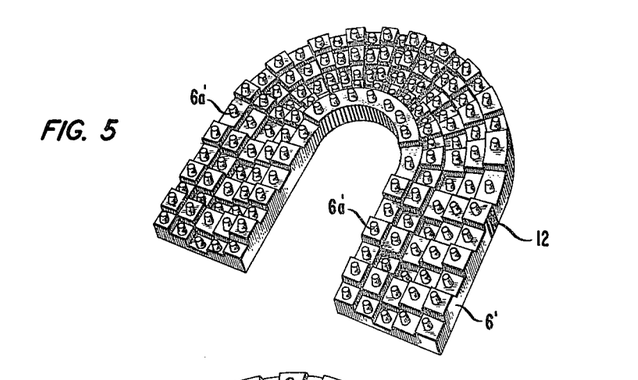
FIG. 5 shows the geometrically patterned underside of a mounting plate, in accordance with the present invention, whose upper surface is constructed for the mounting of a hardened dental model.
Figure 6:
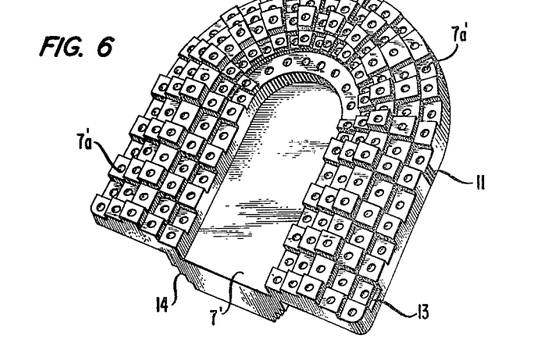
FIG. 6 shows the upper surface of a lower mating plate which is geometrically patterned to mate with the mounting plate underside of FIG. 5.
Figure 7:
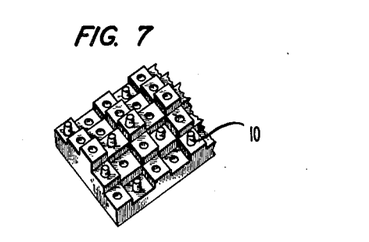
FIG. 7 shows a fragment, a modification of the pattern which may alternatively be employed for the mating surface of either the mounting plate or the lower mating plate.

For convenience in mounting on the articulator, the plates 6' and 7' having intermeshing patterns 6a' and 7a', are each in the shape of an arch, having a maximum width of approximately 2½ inches from the rounded to the flat end, and an overall width of approximately 2⅞ inches across the flat end. The central arched opening is approximately 1⅝ inches long to the point of maximum curvature, and approximately 1⅛ inches across the flat base.

In addition to the interlocking mating surfaces, the mounting plate 6' and the lower mating plate 7' may include on their matching lateral surfaces indexing lines 11 and 12, as well as discernable color coding to assist the operator in quickly matching portions of the mounting plate and lower mating plate which go together. In addition, one or more lateral notches 13 assist the operator by providing a position at which a prying tool can be inserted to pry the closely mated plates 6' and 7' apart.

As a further feature of the invention, the mounting plate 6 (referring again to FIG. 1) may be dimensioned to be slightly broader in extent in its principal plane than lower mating plate 7, so as to provide a slight overhang 6c of, say, ⅛th inch on one or both ot is lateral inner and outer edges to serve as a finger-nail hold for the operator to facilitate in separating plates 6 and 7 when they are in intermeshed relation.

Figure 8:
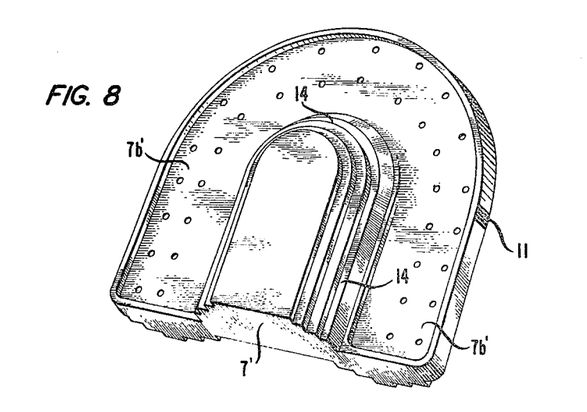
FIG. 8 shows the underside of the lower mating plate of FIG. 6 which has an alternative pattern designed to mate with a matching pattern on the supporting surface of an articulator.

FIG. 8 shows the opposite side 7b' of the plate 7', which contains an arched-shaped projection, including a pattern of concentric steps 14 which key into the intermesh with a modified form of articulator platform which has a matching arch-shaped depression. The articulator platform surface is designed to be secured or may be bonded to the underside 7b' of lower mating plate 7' for increasing the stability of the assemblage.

It will be understood by those skilled in the art that the present invention facilitates quick removal and precise repositioning of individual sections by means of the mating geometric patterns and grooves, indexing and coding and by the grasping ledge that reduces the necessity of the operator to touch the critical surfaces of the actual die reproduction. In addition, the matching mounting and lower mating plates, which may be used for either maxillary or mandibular jaw models, or both together, are fabricated for quick attachment and removal from the articulator platforms. Further, a single section without a geometric pattern on top can be used for articulator indexing, as required for full dentures. Inasmuch as all prefabricated plate halves are interchangeable, it is possible to mate any upper half containing dies with any other lower half of the same type, at any time. This enables the precise transfer of one set of dies to any number of other articulators without disturbing the original mounted relationship of upper to lower jaws.

Although the invention has been disclosed as specifically applied to dentistry, it will be understood that the principles of the present invention have application in many other fields where the use of a precision mating plate system such as described could be utilized or is dictated.

It will be apparent to those skilled in the art that the present invention is not limited to the specific structures disclosed by way of example, but only by the scope of the appended claims.

We claim:

1. A device for processing hardened castings of dental models which comprises a prefabricated precision mating combination including:
   a mounting plate primarily designed for mounting said hardened castings of dental models, said mounting plate having an upper surface and a lower surface, said upper surface constructed to support said castings in bonded relation thereto, and said lower surface being embossed and configured with a first complex geometric pattern including a plurality of repetitive facets;
   a lower mating plate having an upper surface and a lower surface, said upper surface being embossed and configured with a second complex geometric pattern including a plurality of repetitive facets constructed to precisely mate in fixed interlocking registration with the facets of said first geometric pattern when said mounting plate and said lower mating plate are in a preselected spatial relationship, so that the principal planes of said mounting plate and said lower mating plate are locked in substantially parallel relation, whereby said dental castings can be cut and precisely realigned after removal.

2. A device in accordance with claim 1 wherein the lower surface of said lower mating plate is constructed to mate with the platform of an articulator.

3. The combination in accordance with claim 1 wherein the lateral surfaces of said mounting plate and said lower mating plate are marked with corresponding indicia to facilitate orienting them in accordance with said preselected spatial relationship.

4. The combination in accordance with claim 3 wherein said indicia comprise color coding.

5. The combination in accordance with claim 1 wherein said mounting plate is cut into one or more segments, said segments being constructed to be removed from and replaced on said lower mating plate precisely in accordance with said preselected spatial relationship.

6. The combination in accordance with claim 1 wherein the dimensions of said mounting plate are slightly broadened in extent in its principal plane to provide a slight overhang not exceeding about ⅛th of an inch on one or both of its lateral inner and outer edges to serve as a finger-nail hold that permits the operator to gently separate the mounting plate from the mating plate.

7. The combination in accordance with claim 1 wherein said mounting plate and said lower mating plate are formed of a rigid material which is capable of being permanently molded to a tolerance not exceeding about one mil.

8. The combination in accordance with claim 7 wherein said material consists essentially of injection molded high impact polymer which cures to a Rockwell (R) hardness in the range 75 to 150, and has a flexural modulus within the range 200,000 to 600,000 p.s.i.g.

9. The combination in accordance with claim 1 wherein said mounting plate and said lower mating plate are formed of metal.

10. The combination in accordance with claim 1 wherein said mounting plate and said lower mating plate are formed of ceramic.

11. The combination in accordance with claim 1 wherein said mounting plate and said lower mating plate consist essentially of plastic metalized by spraying or coating.

12. A device in accordance with claim 1 wherein said first and second geometric patterns comprise a plurality of perforations to facilitate cleaning and drainage.

13. A system for processing one or more hardened castings for teeth and jaws which comprises in combination:
   an articulator comprising upper and lower platforms hingedly connected to simulate the human jaw;
   a prefabricated precision molded combination including:
   a mounting plate having opposite major surfaces, one said major surface designed to support said castings in bonded relation thereto, and the other said major surface being embossed with a first complex configured geometric pattern having a plurality of repetitive facets;
   a lower mating plate having opposite major surfaces, one said major surface being embossed with a second complex configured geometric pattern having a plurality of repetitive facets constructed to precisely mate with the facets of said first configured geometric pattern in fixed interlocking registration when said mounting plate and said lower mating plate are in a preselected spatial relationship, so that the principal planes of said mounting plate and said lower mating plate are locked in substantially parallel relation;
   the other major surface of said lower mating plate being constructed to be supported on one of the platforms of said articulator.

14. A system in accordance with claim 13 wherein said casting and said mounting plate are cut transversely to said major surfaces to form one or more unique segments, and wherein said unique segments are constructed to be removed and replaced in precise spatial relationship to the remaining portions of said casting.

15. A system in accordance with claim 13 wherein the other major surface of said lower mating plate is configured with a third geometric pattern, and at least one platform of said articulator is configured with a fourth geometric pattern which mates with said third geometric pattern when said lower mating plate is mounted on said platform in a preselected spatial relation.

16. A system in accordance with claim 13 wherein the lateral surfaces of said mounting plate and said lower mating plate are marked with corresponding indicia to facilitate orienting them in accordance with said preselected spatial relationship.

17. The system in accordance with claim 16 wherein said indicia comprise color coding.

18. The system in accordance with claim 13 wherein said mounting plate and said lower mating plate are formed of substantially rigid plastic.

19. The combination in accordance with claim 18 wherein said rigid plastic consists essentially of a thermoplastic or thermosetting material selected from the group consisting of epoxy, arcylic, polyester, nylon, polyacetal or a thermoset resin.

20. The combination in accordance with claim 18 wherein said rigid plastic is a thermoset resin consisting essentially of phenol formaledhyde.

21. The system in accordance with claim 13 wherein said mounting plate and said lower mating plate are formed of metal.

22. The system in accordance with claim 13 wherein said mounting plate and said lower mating plate are formed of ceramic.

23. A method for producing and/or processing model teeth and/or jaws which comprises the steps of:
   forming a hardened casting in a preselected shape;
   attaching said casting to one of the major surfaces of a mounting plate which is one component of a prefabricated precision mating combination comprising said mounting plate and a lower mating plate;
   said mounting plate having a first complex configured prefabricated geometric pattern including a plurality of repetitive facets on its opposite major surface;
   locking said opposite major surface of said mounting plate in fixed interlocking registration with one surface of said lower mating plate which has a second complex geometric pattern including a plurality of repetitive facets which is constructed to intermesh in precise mating relation with the facets of said first complex configured geometric pattern when said mounting plate and said lower mating plate are disposed in a preselected spatial relationship to form said prefabricated precision mating combination, so that said mounting plate and said lower mating plate are locked with their principal planes in substantially parallel relation, whereby said hardened castings can be cut and precisely realigned after removal.

24. The method in accordance with claim 23 which comprises cutting at least one sector of said casting and said mounting plate along a pair of planes transverse to the principal plane of said mounting plate so that said one sector can be removed and replaced on said lower mating plate in the precise position relative to the other parts of said mold from which it was removed.

25. The method in accordance with claim 23 which comprises:
   utilizing an articulator having a prefabricated geometric pattern on at least one platform thereof wherein said lower mating plate has prefabricated on the opposite major surface thereof a pattern which is constructed to mate in intermeshing relation with the pattern on said platform, and mounting said opposite major surface of said lower mating plate in fixed registration with said platform.

26. The method in accordance with claim 23 which comprises coding the lateral edges of said mounting plate and said lower mating plate with matched identifying indicia.

27. The method in accordance with claim 25 which comprises coding the lateral edges of said mounting plate and said lower mating plate with matched color indicia.

28. A device for processing dental models comprising a prefabricated combination for the precision mating of two separate rigid elements in a preselected orientation which comprises:

a first plate having one surface thereof embossed and configured with a first complex geometric pattern having a plurality of repetitive facets, and the opposite surface of said first plate constructed to support said dental models in fixed relation for processing; and a second plate having one surface thereof embossed and configured with a second complex geometric pattern having a plurality of repetitive facets which is substantially the inverse of said first geometric pattern, wherein the facets of said geometric patterns are constructed to precisely mate in fixed registration when said first and second plates are in a preselected spatial relationship so that the major planes of said first and second plates are disposed in substantially parallel relation whereby said dental models can be cut and precisely realigned after removal.

* * * * *

UNITED STATES PATENT AND TRADEMARK OFFICE
CERTIFICATE OF CORRECTION

PATENT NO. : 4,265,619
DATED : May 5, 1981
INVENTOR(S) : John L. Lucki and Alan B. Naha It is certified that error appears in the above–identified patent and that said Letters Patent are hereby corrected as shown below:

Col. 5, line 60, change "is" to ---its---; Col. 6, line 38, change "botton" to ---bottom---; Col. 7, line 26, change "plage" to ---plate---; and Col. 7, line 52, delete "ot is" and insert therefore ---of its---.

Signed and Sealed this

Eleventh Day of August 1981

[SEAL]

Attest:

Attesting Officer

GERALD J. MOSSINGHOFF
Commissioner of Patents and Trademarks